US011583402B2

(12) United States Patent
Baumgartl et al.

(10) Patent No.: US 11,583,402 B2
(45) Date of Patent: Feb. 21, 2023

(54) METHOD FOR TREATING JOINT PAIN

(71) Applicants: William Baumgartl, El Cajon, CA (US); Jack Borbolla, El Cajon, CA (US); Fernando Chavez, El Cajon, CA (US); Charles Puhl, II, El Cajon, CA (US); Dane Reeves, El Cajon, CA (US)

(72) Inventors: William Baumgartl, El Cajon, CA (US); Jack Borbolla, El Cajon, CA (US); Fernando Chavez, El Cajon, CA (US); Charles Puhl, II, El Cajon, CA (US); Dane Reeves, El Cajon, CA (US)

( * ) Notice: Subject to any disclaimer, the term of this patent is extended or adjusted under 35 U.S.C. 154(b) by 81 days.

(21) Appl. No.: 16/930,792

(22) Filed: Jul. 16, 2020

(65) Prior Publication Data
US 2021/0015618 A1 Jan. 21, 2021

Related U.S. Application Data

(60) Provisional application No. 62/874,678, filed on Jul. 16, 2019.

(51) Int. Cl.
A61F 2/28 (2006.01)
A61B 17/68 (2006.01)
A61F 2/46 (2006.01)
A61F 2/30 (2006.01)

(52) U.S. Cl.
CPC ............. *A61F 2/28* (2013.01); *A61B 17/68* (2013.01); *A61F 2/4601* (2013.01); *A61F 2002/2839* (2013.01); *A61F 2002/30062* (2013.01); *A61F 2002/4631* (2013.01)

(58) Field of Classification Search
CPC . A61B 17/16; A61B 17/1635; A61B 17/3205; A61B 17/34; A61B 17/56; A61B 17/68; A61B 2017/564; A61B 17/562; A61F 2/46; A61F 2/4644; A61F 2/28; A61F 2/4601; A61F 2002/4649; A61F 2002/2839; A61F 2002/30062; A61F 2002/4631; A61F 2/30756; A61F 2002/2835; A61F 2002/30764
See application file for complete search history.

(56) References Cited

U.S. PATENT DOCUMENTS

| 5,811,094 | A | 9/1998 | Caplan et al. |
| 6,541,024 | B1 | 4/2003 | Kadiyala et al. |
| 6,863,900 | B2 | 3/2005 | Kadiyala et al. |
| 8,343,480 | B2 | 1/2013 | Long et al. |
| 8,506,983 | B2 | 8/2013 | Mohan et al. |
| 8,858,560 | B2 | 10/2014 | Bradley et al. |
| 8,992,965 | B2 | 3/2015 | Behnam |
| 9,050,178 | B2 | 6/2015 | Barry et al. |
| 9,814,580 | B2 | 11/2017 | Barry et al. |
| 9,980,984 | B2 | 5/2018 | Pettine |
| 2003/0135214 | A1* | 7/2003 | Fetto .................. A61F 2/28 606/76 |
| 2004/0170610 | A1 | 9/2004 | Slavin et al. |
| 2006/0251628 | A1* | 11/2006 | Attawia ............... A61K 38/28 435/372 |
| 2007/0036766 | A1* | 2/2007 | Kevy .................. A61K 35/28 435/378 |
| 2008/0281431 | A1 | 11/2008 | Misses |
| 2016/0317582 | A1* | 11/2016 | Kennedy ............. A61K 35/28 |
| 2017/0335283 | A1 | 11/2017 | Wang et al. |
| 2020/0121328 | A1* | 4/2020 | Lee .................. A61B 17/1615 |

FOREIGN PATENT DOCUMENTS

WO WO 2015/159308 A2 10/2015

OTHER PUBLICATIONS

"Arthritis Related Statistics", Online, URL: <cdc.gov/arthritis/data_statistics/arthritis-related-stats.htm>, accessed Apr. 2021.
"Cortisone Shots", *Mayo Clinic*, accessed online, URL:<https://mayoclinic.org/tests-procedures/cortisone-shots/about/pac-20384794>, Sep. 2019.
"IO-Core Osteochondral Defect Procedure", *Benchmark Biomedical* Brochure, published Mar. 2019.
Alliston et al., "Bone marrow lesions in osteoarthritis: What lies beneath." *J Orthop Res.*, 36(7):1818-1825, 2018.
Arnoldi et al., "Intraosseous Hypertension and Pain in the Knee", *The Journal of Bone and Joint Surgery*, British volume, vol. 57-B, No. 3, 1975.
Astur et al., "Evaluation and Management of Subchondral Calcium Phosphate Injection Technique to Treat Bone Marrow Lesion." *Cartilage*, 10(4):395-401, 2019.
Baumbach et al., "How We Manage Bone Marrow Edema—An Interdisciplinary Approach", *Journal of Clinical Medicine*, 9(2):551, 2020.
Berstock et al., "Mortality After Total Hip Replacement Surgery: A Systematic Review", *Bone Joint Res.*, 3:175182, 2014.
Bonadio et al., "Sunchondroplasty for treating bone marrow lesions in the knee—initial experience." *Rev Bras Ortop.*, 52(3):325-330, 2017.
Chatterjee et al., "Sunchondral Calcium Phosphate is Ineffective for Bone Marrow Edema Lesions in Adults With Advanced Osteoarthritis." *Clin Orthop Relat Res.*, 473(7):2334-2342, 2015.
Cohen et al., "Subchondroplasty for Treating Bone Marrow Lesions." *J Knee Surg.*, 29(7):555-563, 2016.
Collins et al., "Bone Marrow Edema: Chronic Bone Marrow Lesions of the Knee and the Association with Osteoarthritis." *Bull Hosp J Dis (2013).*, 74(1):24-36, 2016.
Colon et al., "Assessment of the injection behavior of commercially available bone BSMs for Subchondroplasty® procedures." *Knee.*, 22(6):597-603, 2015.
Daltro et al., "Efficacy of autologous stem cell-based therapy for osteonecrosis of the femoral head in sickle cell disease: a five year follow-up study." *Stem Cell Res Ther.*,6(1):110, 2015.

(Continued)

*Primary Examiner* — Yashita Sharma
(74) *Attorney, Agent, or Firm* — Norton Rose Fulbright US LLP

(57) ABSTRACT

A method for treating joint pain in a subject is disclosed. The method can include inserting a bone dowel and a first portion of a bone marrow aspirate into a subchondral region of a bone that is part of a joint being treated and introducing a second portion of the bone marrow aspirate into the intraarticular space of the joint being treated.

15 Claims, No Drawings

(56) References Cited

OTHER PUBLICATIONS

Driban et al., "Evaluation of bone marrow lesion volume as a knee osteoarthritis biomarker—longitudinal relationships with pain and structural changes: data from the Osteoarthritis Initiative", *Arthritis Res Ther.*, 15(5):R112, 2013.
Englund et al., "Meniscal pathology on MRI increases the risk for both incident and enlarging subchondral bone marrow lesions of the knee: the MOST Study", *Ann Rheum Dis.*, 69(10):1796-1802, 2010.
Eriksen et al., "Bone marrow lesions: a universal bone response to injury?" *Rheumatology International*, 32:575-584, 2012.
Eriksen; Erik F., Treatment of bone marrow lesions (bone marrow edema). *Bonekey Rep.*, 4:755, 2015.
Etemadifar et al., "The results of core decompression treatment in patients with avascular necrosis of femoral head in patients at Isfahan City educational hospitals in 2010-2011", *Adv Biomed Res.*, 3:93, 2014.
Farr et al., "Quality of Life in Patients with Knee Osteoarthritis: A Commentary on Nonsurgical and Surgical Treatments." *Open Orthop J.*, 7:619-623, 2013.
Felson et al., "Correlation of the Development of Knee Pain with Enlarging Bone Marrow Lesions on Magnetic Resonance Imaging", Arthritis Rheum., 56(9):2986-2992, 2007.
Felson et al., "The association of bone marrow lesions with pain knee osteoarthritis." *Ann Intern Med.*, 134(7):541-549, 2001.
Gangi et al., "Autologous bone marrow cell implantation in the treatment of non-traumatic osteonecrosis of the femoral head: Five year follow-up of a prospective controlled study." *Bone.*, 49(5):1005-1009, 2011.
Goldring et al., "Articular cartilage and subchondral bone in the pathogenesis of osteoarthritis", *Ann N Y Acad Sci.*, 1192:230-237, 2010.
Hernigou et al., "Cell therapy of hip osteonecrosis with autologous bone marrow grafting." *Indian J Orthop.*, 43(1):40-45, 2009.
Hernigou et al., "Treatment of Osteonecrosis With Autologous Bone Marrow Grafting", *Clinical Orthopaedics and Related Research*, 405:14-23, 2002.
Hernigou et al., "Cell therapy versus simultaneous contralateral decompression in symptomatic corticosteroid osteonecrosis: a thirty year follow-up prospective randomized study of one hundred and twenty five adult patients", *International Orthopaedics (SICOT)*, 42:1639-1649, 2018.
Hernigou et al., "Percutaneous autologous bone-marrow grafting for nonunions. Influence of the number and concentration of progenitor cells." *J Bone Joint Surg Am.*, 87(7):1430-1437, 2005.
Hernigou et al., "Subchondral stem cell therapy versus contralateral total knee arthroplasty for osteoarthritis following secondary osteonecrosis of the knee." *Int Orthop.*, 42(11): 2563-2571, 2018.
Hunter et al., "Increase in bone marrow lesions associated with cartilage loss: a longitudinal magnetic resonance imaging study of knee osteoarthritis" *Arthritis Rheum.*, 54(5):1529-1535, 2006.

Kan et al., "Autograft versus allograft in anterior cruciate ligament reconstruction: A meta-analysis with trial sequential analysis." *Medicine (Baltimore).*, 95(38):e4936, 2016.
Lo et al., "Bone marrow lesions and joint effusion are strongly and independently associated with weight-bearing pain in knee osteoarthritis: data from the osteoarthritis initiative", *Osteoarthritis Cartilage*, 17(12):1562-1569, 2009.
Loeser et al., "Osteoarthritis: A Disease of the Joint as an Organ", *Arthritis Rheum.*, 64(6):1697-1707, 2012.
Medvedeva et al., "Repair of Damaged Articular Cartilage: Current Approaches and Future Directions", *International Journal of Molecular Sciences*, 19(2366):1-23, 2018.
Onishi et al., "Osteoarthritis: A Critical Review", *Crit Rev Phys Rehabil Med.*, 24(3-4):251-264, 2015.
Poole, Robin A., "Osteoarthritis as a Whole Joint Disease", *HSS Osteoarthritis Symposium: Frontiers In OA*, 8:4-6, 2012.
Primorac et al., "Knee Osteoarthritis: A Review of Pathogenesis and State-Of-The-Art Non-Operative Therapeutic Considerations", *Genes(Basel)*, 11(8):854, 2020.
Rebolledo et al., "Hitting the Mark: Optimizing the Use of Calcium Phosphate Injections for the Treatment of Bone Marrow Lesions of the Proximal Tibia and Distal Femur." *Arthrosc Tech.*, 7(10):e1013-e1018, 2018.
Saltsman; Kirstie, "Long-term Benefit of Steroid Injections for Knee Osteoarthritis Challenged", *Spotlight on Research*, accessed online, URL:<https://www.niama.nih.gov/newsroom/spotlight-on-research/long-term-benefit-steroid-injections-knee-osteoarthritis-challenged>, Oct. 2017.
Wang et al., "Knee pain as a predictor of structural progression over 4 years: data from the Osteoarthritis Initiative, a prospective cohort study." *Arthritis Res Ther.*, 20(1):250, 2018.
Wluka et al., "Bone marrow lesions predict increase in knee cartilage defects and loss of cartilage volume in middle-aged women without knee pain over 2 years", *Ann Rheum Dis.*, 68(6):850-855, 2009.
"Concepts for Consideration: Sub-Chondral Bone Augmentation—Open & Minimally Invasive Osteo-Core-Plasty," Aspire Newsletter, Aspire Medical Innovation GmbH, 6 pages, Retrieved from the Internet: <https://aspire-medical.eu/newsletter/sub-chondral-bone-augmentation-osteo-core-plasty/>, retrieved Jun. 17, 2022.
Shea, "Autologous Osteo-Core-Plasty—ICRS World Meeting in Macau: Concepts for Consideration: Open & Minimally Invasive Autologous Osteo-Core-Plasty," Retrieved from the Internet: <https://www.linkedin.com/pulse/autologous-osteo-core-plasty-scott-shea/>, published Apr. 17, 2018, retrieved Jun. 17, 2022.
Szwedowski et al., "Osteo-core Plasty: A Minimally Invasive Approach for Subchondral Bone Marrow Lesions of the Knee," Arthroscopy Techniques, 9(11):e1773-e1777, 2020.
YouTube video entitled: "Osteo-Core-Plasty™ treatment with the Marrow Cellution™ System," uploaded Oct. 21, 2019 by user "Aspire Medical Innovation" [retrieved Jun. 17, 2022]. Retrieved from the Internet: <https ://www.youtube.com/watch?v=Qv0qvkP2Bz0>.

\* cited by examiner

METHOD FOR TREATING JOINT PAIN

CROSS-REFERENCE TO RELATED APPLICATIONS

This application claims the benefit of U.S. Provisional Application 62/874,678, filed Jul. 16, 2019. The contents of the referenced application are incorporated into the present application by reference.

STATEMENT REGARDING FEDERALLY FUNDED RESEARCH

None.

BACKGROUND

I. Field of the Invention

The present disclosure relates to methods and compositions for treating inflammation or degeneration of a joint by a combination of (i) core decompression and insertion of a medullary bone dowel and bone marrow, and (ii) intraarticular bone marrow administration.

II. Background of the Invention

When there is damage to the joints that connect bones, as with arthritic conditions, bone inflammation and pain issues can occur. Development of arthritis is a common part of the aging process, age related arthritis is called osteoarthritis (OA), and affects the entire bone. It can cause destruction of the bone or produce abnormal ridges or projections. Osteoarthritis may also be activated by certain diseases. Osteoarthritis is a process that can occur in any joint where the articular cartilage diminishes in thickness as one ages. This process continues until the articular cartilage is gone resulting in bone on bone wear. In most cases this process is associated with gradual, increasing pain, to the point that moving the joint can be unbearable.

OA has long been considered a "wear and tear" disease leading to loss of cartilage. OA used to be considered the sole consequence of any process leading to increased pressure on one particular joint or fragility of cartilage matrix. Progress in molecular biology in recent decades has profoundly modified this paradigm in favor of an "inflammatory" paradigm. Recent reports have shown that subchondral bone may have a substantial role in the OA process, as a mechanical damper, as well as a source of inflammatory mediators implicated in the OA pain process and in the degradation of the deep layer of cartilage. OA is now considered to be a complex disease with inflammatory mediators released by cartilage, bone, and synovium.

Treatments recommended by the American Academy of Orthopedic Surgeons ("AAOS") for osteoarthritis of the knee include the following: weight loss, gentle exercise, anti-inflammatory medications followed by total knee replacement. There remains a need for additional methods and treatments to more effectively treat and reduce pain associated with joint pathologies.

SUMMARY

Embodiments of the invention address the problem of post-surgical pain associated with surgical interventions for treating damaged joints. Certain aspects utilize a combination of decompression (the term "decompression" as used herein refers to a procedure to remove pressure on a structure, e.g., forming a space (e.g., channel) in the bone) and administration (e.g., injection(s)) of a bone dowel and bone marrow aspirate into the decompression, in combination with bone marrow aspirate administration into the intraarticular space to provide attenuated post-surgical pain. In certain aspects, a portion of the bone marrow aspirate is injected into the decompression and a second portion is injected into the intraarticular space—the same bone marrow harvest can be used for both injections, which can be advantageous for ease of administration and the timing of the decompression and both injections. For example, the decompression procedure and both injections can be performed in a shortened period of time (e.g., within 15, 30, 45, 60 minutes to 1, 2, 3, 4, 5, 6 hours of each other), which can reduce surgery time and can decrease patient recovery time by limiting the time the patient is subjected to surgery conditions. In some aspects, the bone dowel and the bone marrow aspirate can be administered to the space simultaneously (e.g., a composition comprising both the bone dowel and bone marrow aspirate) or can be administered sequentially (e.g., the bone dowel can be administered first followed by the bone marrow aspirate or the bone marrow aspirate can be administered first followed by the bone dowel). Sequential administration can be performed within 1, 15, 30, 45, or 60 seconds to 60 minutes). In some aspects, a composition comprising an allograft bone and/or a bone grafting substitute (e.g., demineralized bone, calcium phosphate, mineral composites, ceramics, mineral cements, bioactive glass, proteins, growth factors, or any combination thereof) can also be administered (e.g., injection) into the space. The composition comprising the allograft bone and/or bone grafting substitute can be combined with the bone marrow aspirate, the bone dowel, or both. In other aspects, the composition comprising the allograft bone and/or bone grafting substitute can be administered before or after administration of the bone marrow aspirate or before or after administration of the bone dowel.

Certain embodiments describe methods for treating bone/joint pathologies (e.g., osteonecrosis, arthritis, knee pain, etc.) that result in a more efficient and shortened period of post-surgical pain. The treatment methods include (i) harvesting, independently or concurrently, bone marrow and a bone dowel from iliac crest or similar healthy bone, (ii) drilling or hand drilling into subchondral bone space/area of a lesion or edema for decompression (forming a channel in the subchondral bone), (iii) placing the medullary bone dowel graft and bone marrow aspirate graft/bone marrow aspirate plug/bone marrow aspirate clot in the channel or space formed by decompression (e.g., in step (ii)) in subchondral bone, and (iv) placing bone marrow aspirate into the intraarticular space of the joint being treated. In some aspects, the bone dowel and the bone marrow aspirate can be administered to the subchondral space (e.g., channel) simultaneously (e.g., a composition comprising both the bone dowel and bone marrow aspirate) or can be administered sequentially (e.g., the bone dowel can be administered first followed by the bone marrow aspirate or the bone marrow aspirate can be administered first followed by the bone dowel). Sequential administration can be performed within 1, 15, 30, 45, or 60 seconds to 60 minutes). In some aspects, a composition comprising an allograft bone and/or a bone grafting substitute (e.g., demineralized bone, calcium phosphate, mineral composites, ceramics, mineral cements, bioactive glass, proteins, growth factors, or any combination thereof) can also be administered (e.g., injection) into the space. The composition comprising the allograft bone and/or bone grafting substitute can be combined with the bone marrow aspirate, the bone dowel, or both. In other aspects, the composition comprising the allograft bone and/or bone grafting substitute can be administered before or after administration of the bone marrow aspirate or before or after administration of the bone dowel. Certain aspects can include, but do not require, injecting supporting tendons and/or ligaments of the joint with bone marrow aspirate. As used herein, the term "bone marrow" refers to the cellular tissue found in the hollow interior of mammalian and/or avian bones. Bones of interest for obtaining marrow include long bones, hip bone, breast bone, skull, ribs, vertebrae and shoulder blades, etc. The phrase "bone marrow" or "bone marrow aspirate" encompasses "unprocessed bone marrow" and "processed" bone marrow. Unprocessed bone marrow refers to bone marrow aspirate without any additional processing, such as filtration, density fractionation, or cell sorting. Processed bone marrow refers to bone marrow aspirate that has been further processed such as with filtration, density fractionation, or cell sorting and is suitable for use as a graft. In some aspects, the bone marrow aspirate and/or bone dowel can be combined with an adjuvant or additive. The adjuvant or additive can be a biologically active matrix. Non-limiting examples of biologically active matrix can include bone marrow aspirate (e.g., from the subject), autograft bone, allograft bone, a bone grafting substitute (e.g., demineralized bone, calcium phosphate, mineral composites, ceramics, mineral cements, bioactive glass, proteins, growth factors, or any combination thereof), a placental derived material, an exosome(s), a matrix material (e.g., fibrin, thrombin, or fibrinogen, or any combination thereof), or any combination thereof. Without wishing to be bound by theory the adjuvant or additive is believed to help aid in the healing process of the subject and/or reduce pain in the subject after a method of the present invention has been performed.

Certain embodiments are directed to methods for treating or ameliorating joint pain in a subject. The methods can comprise: (a) inserting a bone dowel and a first portion of a bone marrow aspirate into a subchondral region of a bone that is part of a joint being treated; and (b) introducing a second portion of the bone marrow aspirate into the intraarticular space of the joint being treated. The method can further comprise harvesting the bone dowel from the subject. In certain aspects, the bone dowel is harvested from the iliac crest, vertebra, calcaneus, or tibia of the subject. The bone dowel can have a cylindrical shape and can be 0.5 centimeter (cm) to 4 cm in length. The bone dowel can be about 0.1 to 1 cm in diameter. The method can further comprise harvesting bone marrow aspirate from the subject. In certain aspects, the bone marrow aspirate is harvested via a JAMSHIDI™ needle or other device/technique. The bone marrow aspirate can be harvested from the site, or adjacent to the site where the bone dowel is harvested. The subchondral region of the bone can include a space formed by a decompression procedure. The space can have the shape of a channel having an aspect ratio (width to height) of greater than 1. In some aspects, the bone dowel and the first portion of the bone marrow aspirate can be administered to the subchondral region of the bone simultaneously (e.g., a composition comprising both the bone dowel and bone marrow aspirate) or can be administered sequentially (e.g., the bone dowel can be administered first followed by the bone marrow aspirate or the bone marrow aspirate can be administered first followed by the bone dowel). Sequential administration can be performed within 1, 15, 30, 45, or 60 seconds to 60 minutes). In some aspects, a composition comprising an allograft bone and/or a bone grafting substitute (e.g., demineralized bone, calcium phosphate, mineral composites, ceramics, mineral cements, bioactive glass, proteins, growth factors, or any combination thereof) can also be administered (e.g., injection) into the subchondral region of the bone. The composition comprising the allograft bone and/or bone grafting substitute can be combined with the bone marrow aspirate, the bone dowel, or both. In other aspects, the composition comprising the allograft bone and/or bone grafting substitute can be administered before or after administration of the bone marrow aspirate or before or after administration of the bone dowel. In some aspects, the subject does not have and/or has not been diagnosed with an autoimmune disease. In some aspects, the subject does not have and/or has not been diagnosed with rheumatoid arthritis and/or psoriatic arthritis. In some aspects, the subject is not a smoker (e.g., does not smoke or inhale compositions or products comprising nicotine) and/or is not a nicotine user (e.g., does not smoke or inhale or ingest or inject compositions or products comprising nicotine). "Is not a smoker" and "is not a nicotine user" includes subjects that have not smoked, inhaled, ingested, or injected compositions comprising nicotine at least 4 weeks, 6, weeks, 8 weeks, 10 weeks, 12 weeks, 16 weeks, 20 weeks, 24 weeks, or more, preferably at least 12 weeks, prior to being treated with a method of the present invention.

In certain aspects, the insertion of the bone dowel and the first portion of bone marrow aspirate, and intraarticular injection of the second portion of bone marrow aspirate can be performed within at least, at most, or about 5, 15, 30, 45, 60 minutes to 1, 2, 3, 4, 5, 6 hours of each other, including all values and ranges there between. If desired, the decompression procedure can also be performed within this time frame. In certain aspects, the first portion of bone marrow aspirate and the second portion of the bone marrow aspirate are treated independently. In certain aspects a first portion of bone marrow is dispensed from a bone marrow harvest, and the second portion of bone marrow is dispensed from the same or different bone marrow harvest. The first portion, the second portion, or the first and second portion of bone marrow aspirate can be treated to initiate coagulation. In certain aspects, the joint being treated is a knee joint, shoulder joint, vertebral joint, ankle joint, or hip joint. The subchondral region can be a subchondral edema, an osteonecrosis, or other subchondral lesion. In certain aspects, the subject is diagnosed as having pain or arthritis in the joint being treated or having a degenerative joint disorder. In certain aspects, the subject is experiencing joint pain, such as, but not limited to knee pain.

Certain embodiments are directed to methods for treating joint pain in a subject. The methods can comprise: (a) harvesting a bone dowel and bone marrow aspirate from a source location in the subject; (b) inserting the bone dowel and a first portion of the bone marrow aspirate into a subchondral region of bone forming part of a target joint of the subject; and (c) introducing a second portion of the bone marrow aspirate into the intraarticular space of the target joint. The bone dowel and bone marrow aspirate can be harvested from iliac crest, vertebra, calcaneus, or tibia of the subject. In certain aspects, the bone marrow is harvested via a JAMSHIDI™ needle or other know procedure/device. The insertion of the bone dowel and first portion of bone marrow, and intraarticular injection of the bone marrow can be performed within at least, at most, or about 5 minutes to 6 hours of each other, including all values or ranges there between (e.g., 5, 15, 30, 45, 60 minutes to 1, 2, 3, 4, 5, 6 hours). If desired, the decompression procedure can also be performed within this time frame. In certain aspects, the first portion, second portion, or first and second portion of bone marrow aspirate are treated to initiate coagulation. In certain aspects, the joint is a knee joint, shoulder joint, ankle joint, vertebral joint, or hip joint. The subchondral region can be a subchondral edema or subchondral lesion. The subject can be diagnosed with arthritis in the joint being treated. In certain aspects, the bone dowel has a cylindrical shape and is 0.5 centimeter (cm) to 4 cm in length. In some aspects, the bone dowel and the first portion of the bone marrow aspirate can be administered to the subchondral region of the bone simultaneously (e.g., a composition comprising both the bone dowel and bone marrow aspirate) or can be administered sequentially (e.g., the bone dowel can be administered first followed by the bone marrow aspirate or the bone marrow aspirate can be administered first followed by the bone dowel). Sequential administration can be performed within 1, 15, 30, 45, or 60 seconds to 60 minutes). In some aspects, a composition comprising an allograft bone and/or a bone grafting substitute (e.g., demineralized bone, calcium phosphate, mineral composites, ceramics, mineral cements, bioactive glass, proteins, growth factors, or any combination thereof) can also be administered (e.g., injection) into the subchondral region. The composition comprising the allograft bone and/or bone grafting substitute can be combined with the bone marrow aspirate, the bone dowel, or both. In other aspects, the composition comprising the allograft bone and/or bone grafting substitute can be administered before or after administration of the bone marrow aspirate or before or after administration of the bone dowel.

In one aspect, a method for treating joint pain in a subject is disclosed. The method can include (a) inserting a bone dowel and a first portion of a biologically active matrix into a subchondral region of a bone that is part of a joint being treated and (b) introducing a second portion of the biologically active matrix into the intraarticular space of the joint being treated. The bone dowel can be harvested from a source location in the subject (e.g., autograft bone dowel). The at least a portion of the first portion of the biologically active matrix can be harvested from a source location in the subject. The biologically active matrix can include bone marrow aspirate (e.g., from the subject), autograft bone, allograft bone, a bone grafting substitute (e.g., demineralized bone, calcium phosphate, mineral composites, ceramics, mineral cements, bioactive glass, proteins, growth factors, or any combination thereof), a placental derived material, an exosome(s), a matrix material (e.g., fibrin, thrombin, or fibrinogen, or any combination thereof), or any combination thereof. In some aspects, the bone dowel and the first portion of the biologically active matrix can be administered to the subchondral region of the bone simultaneously (e.g., a composition comprising both the bone dowel and first portion of the biologically active matrix) or can be administered sequentially (e.g., the bone dowel can be administered first followed by the first portion of the biologically active matrix or the first portion of the biologically active matrix can be administered first followed by the bone dowel). Sequential administration can be performed within 1, 15, 30, 45, or 60 seconds to 60 minutes).

Also disclosed in the context of the present invention are aspects 1 to 38. Aspect 1 includes a method for treating joint pain in a subject, the method comprising: (a) inserting a bone dowel and a first portion of a bone marrow aspirate into a subchondral region of a bone that is part of a joint being treated; and (b) introducing a second portion of the bone marrow aspirate into the intraarticular space of the joint being treated. Aspect to is the method of aspect 1, further comprising harvesting the bone dowel from the subject. Aspect 3 is the method of aspect 2, wherein the bone dowel is harvested from an iliac crest, vertebra, calcaneus, or tibia of the subject. Aspect for is the method of any one of aspects 1 to 3, further comprising harvesting bone marrow aspirate from the subject. Aspect 5 is the method of aspect 4, wherein the bone marrow aspirate is harvested via a JAMSHIDI™ needle. Aspect 6 is the method of any one of aspects 4 or 5, wherein the bone marrow aspirate is harvested from the site, or adjacent to the site where the bone dowel is harvested. Aspect 7 is the method of any one of aspects 1 to 6, wherein insertion of the bone dowel and the first portion of bone marrow aspirate, and intraarticular injection of the second portion of bone marrow aspirate are performed within 5 minutes to 6 hours of each other, preferably within 5 minutes to 4 hours of each other, or more preferably within 5 minutes to 2 hours of each other. Aspect 8 is the method of any one of aspects 1 to 7, wherein the first portion of bone marrow aspirate is treated to initiate coagulation. Aspect 9 is the method of any one of aspects 1 to 8, wherein the joint is a knee joint, shoulder joint, ankle joint or hip joint. Aspect 10 is the method of any one of aspects 1 to 9, wherein the subchondral region is a subchondral edema or subchondral lesion. Aspect 11 is the method of any one of aspects 1 to 10, wherein the subject is diagnosed as having arthritis in the joint being treated or a degenerative joint disorder. Aspect 12 is the method of any one of aspects 1 to 11, wherein the bone dowel has a cylindrical shape and is 0.5 centimeter (cm) to 4 cm in length. Aspect 13 is the method of any one of aspects 1 to 12, wherein: prior to step (a), a space is formed via decompression in the subchondral region of the bone that is part of the joint being treated; and the bone dowel and the first portion of the bone marrow aspirate is inserted into the space. Aspect 14 is the method of any one of aspects 1 to 13, wherein step (a) further comprises inserting an allograft bone and/or a bone grafting substitute into the subchondral region of the bone. Aspect 15 is the method of aspect 14, wherein the bone grafting substitute is inserted into the subchondral region of the bone. Aspect 16 is the method of aspect 15, wherein the bone grafting substitute comprises demineralized bone, calcium phosphate, a mineral composite, a ceramic, a mineral cement, a bioactive glass, a protein, a growth factor, or any combination thereof).

Aspect 17 is a method for treating a joint pain in a subject, the method comprising: (a) harvesting a bone dowel and bone marrow aspirate from a source location in the subject; (b) inserting the bone dowel and a first portion of the bone marrow aspirate into a subchondral region of bone forming part of a target joint of the subject; and (c) introducing a second portion of the bone marrow aspirate into the intraarticular space of the target joint. Aspect 18 is the method of aspect 17, wherein the bone dowel and bone marrow aspirate are harvested from iliac crest, vertebra, calcaneus, or tibia of the subject. Aspect 19 is the method of any one of aspects 17 to 18, wherein the bone marrow is harvested via a JAMSHIDI™ needle. Aspect 20 is the method of any one of aspects 17 to 19, wherein insertion of the bone dowel and first portion of bone marrow, and intraarticular injection of the bone marrow are performed within 5 minutes to 6 hour of each other. Aspect 21 is the method of any one of aspects 17 to 20, wherein the first portion of bone marrow aspirate is treated to initiate coagulation. Aspect 22 is the method of any one of aspects 17 to 21, wherein the joint is a knee joint, shoulder joint, ankle joint, vertebral joint, or hip joint. Aspect 23 is the method of any one of aspects 17 to 22, wherein the subchondral region is a subchondral edema or subchondral lesion. Aspect 24 is the method of any one of aspects 17 to 23, wherein the subject is diagnosed as having arthritis in the joint or a degenerative joint disorder being treated. Aspect 25 is the method of any one of aspects 17 to 24, wherein the bone dowel has a cylindrical shape and is 0.5 centimeter (cm) to 4 cm in length. Aspect 26 is the method of any one of aspects 17 to 25, wherein: prior to step (b), a space is formed via decompression in the subchondral region of the bone that is part of the joint being treated; and the bone dowel and the first portion of the bone marrow aspirate is inserted into the space. Aspect 27 is the method of any one of aspects 17 to 26, wherein step (b) further comprises inserting an allograft bone and/or a bone grafting substitute into the subchondral region of the bone. Aspect 28 is the method of aspect 27, wherein the bone grafting substitute is inserted into the subchondral region of the bone. Aspect 29 is the method of aspect 28, wherein the bone grafting substitute comprises demineralized bone, calcium phosphate, a mineral composite, a ceramic, a mineral cement, a bioactive glass, a protein, a growth factor, or any combination thereof.

Aspect 30 is a method for treating joint pain in a subject, the method comprising: (a) inserting a bone dowel and a first portion of a biologically active matrix into a subchondral region of a bone that is part of a joint being treated; and (b) introducing a second portion of the biologically active matrix into the intraarticular space of the joint being treated. Aspect 31 is the method of aspect 30, wherein the bone dowel is harvested from a source location in the subject. Aspect 32 is the method of any one of aspects 30 to 31, wherein at least a portion of the first portion of the biologically active matrix is harvested from a source location in the subject. Aspect 33 is the method of any one of aspects 30 to 32, wherein the biologically active matrix comprises bone marrow aspirate. Aspect 34 is the method of any one of aspects 30 to 33, wherein the biologically active matrix comprises autograft bone or allograft bone. Aspect 35 is the method of any one of aspects 30 to 34, wherein the biologically active matrix comprises a bone grafting substitute. Aspect 36 is the method of aspect 35, wherein the bone grafting substitute comprises demineralized bone, a calcium phosphate, a mineral composite, a ceramic, a mineral cement, a bioactive glass, a protein, a growth factor, or any combination thereof. Aspect 37 is the method of any one of aspects 30 to 36, wherein the biologically active matrix comprises a placental derived material, an exosome(s), a matrix material, or any combination thereof. Aspect 38 is the method of aspect 37, wherein the matrix material comprises fibrin, thrombin, fibrinogen, or any combination thereof.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The terms "subchondral bone plate" and "cortical bone plate" are used herein interchangeably, and refer to the thin cortical lamella lying immediately beneath the cartilage.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of"

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Articular cartilage is both aneural and avascular. As such, cartilage may be incapable of directly generating pain, stiffness, or any of the symptoms that patients with bone disease describe. In contrast, the subchondral bone, periosteum, periarticular ligaments, periarticular muscle, synovium, and joint capsule are all richly innervated and can be the source of nociception in bone disease. Furthermore, biochemical communication between subchondral bone, articular cartilage, and joint space can be associated with the initiation and progression of bone disease linked to bone degeneration, in terms of pain, function, and pathology. Alterations of any tissue will modulate the properties and functions of other parts of the osteochondral junction.

During bone disease linked to bone degeneration, functional units of joints comprising cartilage and subchondral bone can undergo remodeling processes to adapt to local biochemical and biological signals. Changes in cartilage and subchondral bone are not merely secondary manifestations of bone disease but are active components of the disease, contributing to its severity. The close proximity of cartilage and subchondral bone provides an ample opportunity to induce physical and functional alteration in each other. As a result of the biochemical processes in the joint space and subchondral bone, a degenerative biochemical response is initiated which accelerates as biomechanical changes begin to manifest themselves in patients with bone disease. Treatment of both compartments, subchondral compartment and joint space, can be useful in reducing joint pain.

When there is damage to the joints that connect bones, as with arthritic conditions, bone inflammation and pain issues can occur. Osteoarthritis can affect the entire bone, and can cause destruction of the bone or produce abnormal ridges or projections. Osteoarthritis may also be activated by certain diseases. Successful treatment of inflammation depends on treating the cause. If it is produced by an infection, symptoms may continue until the infection is eliminated. With health conditions that cause permanent damage to the joints or bones, a comprehensive exercise and strengthening program may help alleviate painful symptoms and may also aid in the restoration of range of motion. In severe cases, surgical correction of the bone may be necessary. Methods described herein include surgical techniques that are combined to create a favorable and novel treatment for patients.

I. Methods for Treating Joint Pathologies

Certain embodiments are directed to methods for treating joint pain in a subject. The methods can comprise:(a) inserting a bone dowel and a first portion of a bone marrow aspirate into a subchondral region of a bone that is part of a joint being treated; and (b) introducing a second portion of the bone marrow aspirate into the intraarticular space of the joint being treated. In certain aspects the method described herein can be used in conjunction with arthroscopy and other compatible therapeutic methods.

A. Decompression or Core Decompression

Decompression is a surgical procedure that involves forming a space (e.g., channel), e.g., surgical drilling, in the area of dead or damaged bone near the joint, reducing pressure, allowing for increased blood flow, and slowing or stopping bone and/or joint destruction. Decompression is commonly performed to treat osteonecrosis and other conditions. Typically, imaging is done prior to and or during the procedure to help identify the areas of dead bone and the location for decompression. Decompression stimulates healthy bone production and the development of new blood vessels. Typically, the patient is placed under general anesthesia and is then prepared and draped in an aseptic manner. Under fluoroscopic guidance a core of bone is removed, which may form a channel. After the procedures the skin is closed with a suture(s) and a sterile dressing applied. Following surgery, patients can be discharged on the same day and are allowed partial weight-bearing for a time followed by full weight-bearing at a later time.

B. Materials Harvesting

Bone marrow and medullary bone dowel are harvested from a healthy donor site in a patient (e.g., the iliac crest, vertebral body, or tibia).

1. Bone Dowel

The bone dowel can be obtained using a bone dowel harvesting instrument(s) or similar device(s). The iliac crest provides several donor sites for bone graft harvesting. Besides the posterior iliac crest, one major donor site is the area around the anterior lip of the iliac crest. The drill depth can be approximately 10 to 25 mm. The diameter can be between 1 and 10 mm. A guide wire and protection sleeve can be positioned. Once an incision is made above the iliac crest, a T-handle can be used to insert the guide wire to depth. For a minimally invasive technique, a trocar can be used to insert the protection sleeve over the guide wire to the iliac crest. Removing the trocar provides access for bone harvesting over the guide wire and the protection sleeve.

The appropriate trephine attachment can be mounted onto the holder, and the holder shoved over the guide wire. The holder can be inserted in connection with the guide wire. Drilling can be performed with oscillating movements. To penetrate hard cortical bone, it can be useful to use a hammer. After drilling the holder can be removed. In most cases, the bone dowel will be in the trephine attachment. However, should the dowel still be in the iliac crest, the trephine attachment can be removed and the appropriate extraction attachment mounted. The holder can be slid over the guide wire and a hammer can be used to insert the extractor until a limited depth is reached. In certain instances, the graft dowel can be broken free by turning the holder slowly until a cracking noise is heard or no more resistance is felt in turning. The holder can be removed and both the bone dowel and the guide wire may remain in the extraction attachment.

2. Bone Marrow

In an adjacent or same spot on the donor site, bone marrow aspirate can be harvested using a bone marrow JAMSHIDI™ needle or similar device. In certain aspects about 10, 20, 30, 40, 50, 60, 70, 80 mL or more of aspirate can be drawn. A bone marrow aspiration trochar can be used to harvest bone marrow. After obtaining the harvested bone marrow the bone marrow can be processed using filtration, concentration through centrifugation, coagulation, or any combination thereof. Coagulation can be induced using calcium chloride and thrombin, calcium gluconate, fibrin glue, manual manipulation, or autologous thrombin.

For example, with the patient positioned in a supine position on the operating table, the iliac crest can be surgically prepped and draped. A combination of conscious sedation and local anesthesia (1 e.g., % lidocaine) can be used. Prior to aspiration, an 11-Gauge Bone Access Needle (Medtronic, Inc) or similar device can be flushed with a heparin solution. Using a stab incision, the bone access needle can be inserted and advanced through the periosteum of the Anterior Superior Iliac Spine. In certain embodiments a trephine needle and 60 cc syringe can be used to remove the marrow. The trephine needle can be inserted percutaneously through the skin until the bony surface of the iliac crest is felt. In certain instances a mallet can be used to drive the needle to a depth of 3-4 cm into the crest. After the periosteum is pierced, the driver and stylet can be removed and a syringe containing a heparin dilution can be used to aspirate bone marrow. The total amount of bone marrow harvested (BMA) can be 10 to 80 mL. Following bone marrow aspiration, the bone access needle can be withdrawn, pressure can be applied to the skin entry site, followed by dressing application. Following extraction, the aspirate can be transferred to sterile tubes and processed under sterile conditions.

In one aspect, the bone marrow is autologous bone marrow aspirate (BMA). An amount of bone marrow aspirate can be mixed with an amount of a pre-mixture. The pre-mixture can include anticoagulant(s), sugar(s) such as dextrose, and a buffer such as phosphate buffered saline (PBS). Typically, the iliac crest, and more typically the posterior iliac crest, is where bone marrow aspirate may be harvested in a surgical setting, however any suitable area where BMA may be extracted may be used.

C. Sub-Chondral Treatment

The joint being treated can be subjected to decompression. The bone dowel and a portion of the bone marrow can then be guided into subchondral channels, lesions, deficits, or edemas in the bone below or above the joint space to fill and replace lost or missing bone tissue with the medullary bone dowel and bone marrow graft. This can be done through use of precise guidance via fluoroscopy in an operating room (OR) setting. Once the lesion/deficit has been grafted with dowel/bone marrow, the remaining bone marrow can be introduced into the intraarticular space to address degeneration in the joint space.

D. Treatment of Intraarticular Space

After the lesion/deficit has been grafted with dowel/bone marrow, the remaining bone marrow can be introduced into the intraarticular space to address degeneration in the joint space. This may be done under ultrasound guidance, fluoroscopy, or no guidance at all. The subchondral bone and the intraarticular space can be treated in the same patient at the point of care on the same day with bone marrow in joint space combined with marrow/medullary dowel to fill the lesion in the subchondral bone. By addressing the lesions in the subchondral bone below and above, the patient can experience greater pain relief and increased satisfaction and function. All injections can be performed using an anterolateral approach to the knee joint. Following injection, the knee joint can be passively manipulated throughout its range of motion to disseminate the fluid throughout the joint.

II. Methods of Treatment

The compositions and methods disclosed herein are useful for the treatment of degenerate bone in a patient. In some embodiments, the degenerate bone is disposed in an affected area of bone. In some embodiments, the affected area or bone is a region of bone that exhibits inflammatory and/or degradative changes as a result of inflammatory and/or non-inflammatory mediators. In some embodiments, the methods and compositions disclosed herein are useful for the treatment of bone disease in a patient, particularly bone diseases associated with joints.

In some embodiments, the methods and compositions disclosed herein are useful for the treatment of joint pain. In some embodiments, the methods and compositions disclosed herein are useful for the treatment of bone pain. In some embodiments, the methods and compositions disclosed herein are useful for the treatment of arthritic pain. In some embodiments, the affected area is a knee. In further embodiments, the affected area is a hip. In further embodiments, the affected area is a shoulder. In further embodiments, the affected area is an ankle. In further embodiments, the affected area is a wrist. In further embodiments, the affected area is an elbow. In further embodiments, the affected area is a vertebrae. In further embodiments, the affected area is a hand.

In some embodiments, the methods and compositions disclosed herein are useful for the treatment of arthritis in an affected joint. In some embodiments, the arthritis is OA. In some embodiments, the arthritis is rheumatoid arthritis. In some embodiments, the affected joint is a knee. In further embodiments, the affected joint is a hip. In further embodiments, the affected joint is a shoulder. In further embodiments, the affected joint is an ankle. In further embodiments, the affected joint is a wrist. In further embodiments, the affected joint is an elbow. In further embodiments, the affected joint is a vertebrae. In further embodiments, the affected joint is a joint proximal to a hand.

In some embodiments, the methods and compositions disclosed herein are useful for the treatment of avascular necrosis. In some embodiments, the affected joint is a knee. In further embodiments, the affected joint is a hip. In further embodiments, the affected joint is a shoulder. In further embodiments, the affected joint is an ankle. In further embodiments, the affected joint is a wrist. In further embodiments, the affected joint is an elbow. In further embodiments, the affected joint is a vertebrae. In further embodiments, the affected joint is a joint proximal to a hand.

In some embodiments, the methods and compositions disclosed herein are useful for the treatment of focal osteochondral defects in an affected bone. In some embodiments, the affected bone is a femoral condyle. In some embodiments, the affected bone is a humeral head. In some embodiments, the affected bone is a talus. In some embodiments, the affected bone is a capitellum of the humerus. In some embodiments, the affected bone is an elbow. In some embodiments, the affected bone is a wrist. In some embodiments, the affected bone is a hand bone. In some embodiments, the affected bone is a toe. In some embodiments, the methods and compositions disclosed herein are useful for the treatment of a femoral head. In some embodiments, the methods and compositions disclosed herein are useful for the treatment of an acetabulum. In some embodiments, the methods and compositions disclosed herein are useful for the treatment of a tibial plateau.

Accordingly, in some embodiments, the methods disclosed herein comprise the step of decompressing or aspirating the affected area. In some embodiments, the step of obtaining access to the affected area provides for decompression of the affected area.

In some embodiments, patients can maintain partial weight bearing and use ambulatory aids post-operatively. In some embodiments, full weight bearing is permitted post-operatively. In some embodiments, post-intervention physical therapy is performed. In some embodiments, patients may have routine post intervention care, observation, and follow-up.

III. Kits

In some embodiments, the kit comprises tools for harvesting bone dowel and bone marrow, as well deploying the same to treat a degenerative joint. In some embodiments, the tools are adapted to provide a channel in the bone into which the bone dowel and bone marrow is inserted. In some embodiments, the kit comprises a bone filler to seal the open end of the channel in the bone in which the material is inserted.

In some embodiments, at least a portion of the kit and its contents are sterile. In some embodiments, the sterility comprises a condition in which an object has a sterility assurance level (SAL) of $10^{-3}$ or less. In further embodiments, the sterility comprises a condition in which an object has a SAL of $10^{-6}$ or less. In some embodiments, the SAL can be determined in accordance with current FDA guidelines for medical devices. In some embodiments, the syringes are sterile.

EXAMPLES

Aspects of the present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Materials and Methods

Overall Patient Population: Twenty four (24) patients were treated in a similar manner described in the below Procedure section. All twenty four (24) patients in this study had knee(s) pain from osteoarthritis. All patients were candidates for a total knee replacement procedure but did not undergo such procedure prior to being treated with the methods of the present invention. The total time for the procedures described below in the Procedure section varied between 45 minutes to 120 minutes with an average time of about 60 minutes.

Overall Methodology: Methodology combines: 1) core decompression of subchondral lesion/edema, 2) fluoroscopy-guided bone grafting of subchondral lesions/edemas (present on MRI) with medullary bone dowels and marrow harvested from iliac crest, and 3) placement of intra-articular bone marrow cells. The following includes a description of one (1) patient ("Patient 1") and the materials and methods used to treat Patient 1. Similar procedures were also performed on an additional (23) patients. Pain study results of all twenty four (24) patients are provided in the Results section.

Patient 1: The patient presented with complaints of chronic knee pain. Previous imaging has confirmed diffuse knee compartment chondral degeneration as well as MRI-confirmed subcortical/subchondral degeneration of the bone of both the lateral femoral and tibial compartments. The patient had osteoarthritis. The patient failed past treatment with conservative measures, including physical therapy, anti-inflammatory medication, and intra-articular injections. The patient's pain persisted in spite of these conservative care techniques, and, in fact, was getting progressively worse over time. The patient presented for an implantation of bone graft tissue autograft.

Procedure: Patient 1 was initially placed in a prone position. The Left posterior-superior iliac spine was prepped with alcohol, and then Chloroprep. 300 cc of 0.25% Lidocaine Tumescent was prepared, with 1 gm Cephazolin added. Attention was initially directed to the posterior pelvis, where a bone marrow and bone graft was obtained. After numbing the skin with tumescent, Fluoroscopy was used to visualize the posterior-superior iliac spine. The skin tract and periosteum was numbed with 80 cc of tumescent. An entry site was selected over the posterior-superior iliac spine using fluoroscopic guidance, and an entry incision through the skin was made with a #15 blade. Using a bone harvest kit, the coring tool was placed on the periosteal surface, and cored a depth of approximately 3 cm. An approximately 3 mm diameter, 2.5 cm long bone plugN core was harvested, and set aside for further grafting. A second bone dowel plug was similarly obtained from a second adjacent site. The harvesting tool was then removed. A third entry was used to harvest bone marrow. Using the bone harvest device and protocol, the PSIS was identified under image guidance, and the harvester was then inserted it through the skin portal, and advanced to contact with the PSIS. The harvester was then advanced through the cortex, angling to match the slope of the iliac crest. The syringe was removed and the blunt-tipped harvesting cannula was inserted and then advanced down into the marrow cavity to maximum depth. The harvester was then secured per protocol. The central stylet was removed and two 10 cc syringes were attached, each containing (¼ cc) 500 units heparin per standardized protocol. 20 cc of high density-marrow, in total, was aspirated, and set aside for further grafting. An additional 60 cc of bone marrow was aspirated through the device, anticoagulated with 1000 units Heparin. The syringe was removed, and the harvester was extracted. The skin was cleansed, and the wound was dressed with a steri-strip, sterile gauze, and Tegaderm. The patient tolerated the procedure well and there were no complications.

The second stage extracted marrow bone tissue was then processed in a Centrifuge, using their blood centrifugal separating device, and concentrated to 15 cc volume of the cell rich graft. An additional 15 cc of cell-poor product was obtained. A two spin cycle was used, first 3800 rpm at 1.5 minutes for the first stage, followed by 7 minutes at 3800 rpm for the second stage.

Next, the patient was turned supine. After examining the knee under fluoro, the skin was first marked, and then prepped with alcohol and Chloroprep, and draped sterilely. The knee was placed on a foam wedge to elevate the knee. A combination of AP and lateral views were used to image the knee, using Fluoroscopy. The knee was marked for injection.

A set of geniculate blocks were first performed. At the marked levels, a 23 ga, 3.5" spinal needle was advanced under fluoroscopic guidance using an anterior approach, to block the genicular nerves bilaterally at the lateral and medial distal portions of the Femur. One additional needle was placed the proximal medial side of the tibia. Fluoroscopy was used to guide the needle placement. After confirming correct needle placement, 30 cc of additional Tumescent anesthestic was placed at each of the 3 locations.

A Subchondroplasty was initially performed marking the femur, medially, at the mid-femural shaft point. A total of 60 cc of tumescent was used to numb the skin and miditibial periosteum. A 15 blade was then to create the skin entry. The coring tool with a stylette was advanced into the middle compartment of the bone by hand drilling. Following this, the previously-harvest bone plug was placed through the cutting tool into the medial subchondral surface, and grafted into place in the lateral compartment. A solution was prepared by mixing 5000 units of Thrombin in 5 cc of 10% Calcium Chloride. 1 cc of this solution was mixed with the previously-harvested 10 cc of direct bone marrow, and allowed to partially coagulate. Following this, the coagulated marrow was grafted into place, over the bone dowel plug. The cutting tool and bone placement tools were removed, and the wound closed with a 4-0 chromic gut, steristrips and Mastisol. The subchondroplasty was additionally performed at the top of the tibial from a medial approach. The second bone plug was grafted into place, with additional coagulated marrow placed over the graft. The second wound was also closed with 4-0 chromic gut, steristrips and Mastisol.

Next, a 20 ga Touhy was advanced under fluoroscopic guidance, using a medial-inferior anterior entry by loss of resistance to fluid pressure towards the femoral notch. Successful placement on the first try was achieved. The needle placement was verified by injecting 1 cc of ISOVUE 200 dye. Dye is seen filling the intra-articular surface. The knee was injected with 10 mg Preservative-Free Morphine for post-op pain control. Additional 20 ga Touhy needles were placed medially and laterally to the knee joint, near the joint line to treat the meniscus medially and laterally.

Following this, 12 cc of the previously processed cell-rich bone marrow tissue was grafted into place in to the knee joint to perform a percutaneous image-guided femuroplasty. Appropriate displacement of dye was confirmed. The cell-poor bone marrow graft was divided equally between the medial and lateral joint lines, and grafted to place, preceded by 1.5 cc of cell rich graft. All needles were removed, and the patient was then returned to the recovery room. The patient was subsequently discharged home in good condition.

A successful knee subchondroplasty bone graft and femuroplasty was performed on the knee as described. This was performed for to seal, fill, and replace lost cartilage tissue, and repair ligamentous/meniscal tissues, as well as to treat subchondral bone defects. There were no initial complications.

Results

Patient 1 and an additoinal twenty three (23) patients with knee pain associated with osteoarthritis, all candidates for total joint replacement, underwent a joint salvage procedure involving core decompression of the subchondral area of damage, supplemented by a bone core and bone marrow graft of the subchondral space. This was augmented by grafting the bone marrow into the intraarticular joint space, as well as optionally grafting to supporting ligaments. Twenty one (21) of the twenty four (24) patients treated experienced acceptable relief of their pain, and have maintained their pain relief in the initial months following the procedure. Three (3) patients did not maintain their relief. Their history was notable for one (1) patient with rheumatoid arthritis (RA), and two (2) patients with marked valgus deformity of their joint.

The procedure overal methodology described above was remarkable for the early pain relief, despite being a more invasive procedure than simple intraarticular grafting. Most patients experienced marked pain relief in the first week. Over 90% of the patients were pain free two weeks after the procedure. Pain was subjectively measured by asking the patient to provide level of pain on a 1 to 10 scale. Without wishing to be bound by theory, it is believed that by treating the subchondral disease in addition to the intra-articular disease, investigators believe that the root of the pain is being addressed. Placement of structural medullary dowels and marrow clot helps to fill and replace bone lost to degenerative joint disease.

The procedure also shows marked success in reducing pain in patients despite having very advanced arthritis, including complete loss of articular cartilage. Severe cartilage loss was not a limitation to success in the procedure, however poorer outcomes were associated with rheumatologic disease and marked ligamentus instability/joint deformity.

Further, and because the procedure involves a combination of accepted bone grafting and core decompressiion processes, the procedure has the potential to be covered by standard insurance. Initial data suggests this procedure may be a suitable alternative to total joint replacement.

The invention claimed is:

1. A method for treating joint pain in a subject, the method comprising:
    (a) harvesting a bone dowel from an iliac crest, vertebra, calcaneus, or tibia of the subject;
    (b) harvesting a bone marrow aspirate from the subject, wherein the bone marrow aspirate is harvested from the site, or adjacent to the site, where the bone dowel is harvested;
    (c) inserting the bone dowel and a first portion of the bone marrow aspirate into a subchondral region of a bone that is part of a joint being treated; and
    (d) introducing a second portion of the bone marrow aspirate into the intraarticular space of the joint being treated,
    wherein prior to step (c), a space is formed via decompression in the subchondral region of the bone that is part of the joint being treated, and the bone dowel and the first portion of the bone marrow aspirate are inserted into the space.

2. The method of claim 1, wherein the bone marrow aspirate is harvested via a needle.

3. The method of claim 1, wherein insertion of the bone dowel and the first portion of bone marrow aspirate, and intraarticular injection of the second portion of bone marrow aspirate are performed within 5 minutes to 6 hours of each other, preferably within 5 minutes to 4 hours of each other, or more preferably within 5 minutes to 2 hours of each other.

4. The method of claim 1, wherein the first portion of bone marrow aspirate is treated to initiate coagulation.

5. The method of claim 1, wherein the joint is a knee joint, shoulder joint, ankle joint or hip joint.

6. The method of claim 1, wherein the subchondral region is a subchondral edema or subchondral lesion.

7. The method of claim 1, wherein the subject is diagnosed as having arthritis in the joint being treated or is diagnosed as having a degenerative joint disorder.

8. The method of claim 1, wherein the bone dowel has a cylindrical shape and is 0.5 centimeter (cm) to 4 cm in length.

9. The method of claim 1, wherein step (c) further comprises inserting an allograft bone and/or a bone grafting substitute into the subchondral region of the bone.

10. The method of claim 9, wherein the bone grafting substitute is inserted into the subchondral region of the bone.

11. The method of claim 10, wherein the bone grafting substitute comprises demineralized bone, calcium phosphate, a mineral composite, a ceramic, a mineral cement, a bioactive glass, a protein, a growth factor, or any combination thereof.

12. A method for treating a joint pain in a subject, the method comprising:
   (a) harvesting a bone dowel and bone marrow aspirate from a source location in the subject;
   (b) inserting the bone dowel and a first portion of the bone marrow aspirate into a subchondral region of bone forming part of a target joint of the subject; and
   (c) introducing a second portion of the bone marrow aspirate into the intraarticular space of the target joint.

13. The method of claim 12, wherein the bone dowel and bone marrow aspirate are harvested from iliac crest, vertebra, calcaneus, or tibia of the subject.

14. The method of claim 12, wherein step (b) further comprises inserting an allograft bone and/or a bone grafting substitute into the subchondral region of the bone, wherein the bone grafting substitute comprises demineralized bone, calcium phosphate, a mineral composite, a ceramic, a mineral cement, a bioactive glass, a protein, a growth factor, or any combination thereof.

15. A method for treating joint pain in a subject, the method comprising:
   (a) inserting a bone dowel and a first portion of a biologically active matrix into a subchondral region of a bone that is part of a joint being treated; and
   (b) introducing a second portion of the biologically active matrix into the intraarticular space of the joint being treated,
   wherein the bone dowel and at least a portion of the biologically active matrix are both harvested from the subject.

* * * * *

UNITED STATES PATENT AND TRADEMARK OFFICE
CERTIFICATE OF CORRECTION

PATENT NO. : 11,583,402 B2
APPLICATION NO. : 16/930792
DATED : February 21, 2023
INVENTOR(S) : William Baumgartl et al.

It is certified that error appears in the above-identified patent and that said Letters Patent is hereby corrected as shown below:

In the Claims

In Claim 12, Column 17, Line 17, delete "sub ject;" and insert --subject;-- therefor.

Signed and Sealed this
Ninth Day of May, 2023

Katherine Kelly Vidal
*Director of the United States Patent and Trademark Office*